United States Patent
Kim et al.

(12)

(10) Patent No.: US 10,100,286 B2
(45) Date of Patent: Oct. 16, 2018

(54) SYSTEMS AND METHODS OF DISSOCIATING AGGREGATE SPHERES OF CELLS

(71) Applicant: The Board of Trustees of the University of Alabama, Tuscaloosa, AL (US)

(72) Inventors: Yonghyun Kim, Northport, AL (US); David A. Dozier, Tuscaloosa, AL (US); Ursula L. Triantafillu, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 228 days.

(21) Appl. No.: 14/744,200

(22) Filed: Jun. 19, 2015

(65) Prior Publication Data

US 2015/0368619 A1     Dec. 24, 2015

Related U.S. Application Data

(60) Provisional application No. 62/015,082, filed on Jun. 20, 2014.

(51) Int. Cl.
*C12N 5/09* (2010.01)
*C12M 1/00* (2006.01)
*G01N 1/28* (2006.01)

(52) U.S. Cl.
CPC .......... *C12N 5/0693* (2013.01); *C12M 47/04* (2013.01); *C12N 2509/10* (2013.01); *G01N 1/286* (2013.01)

(58) Field of Classification Search
CPC .. C12M 47/04; C12N 2509/10; C12N 5/0693; G01N 1/286
See application file for complete search history.

(56) References Cited

U.S. PATENT DOCUMENTS

| | | | |
|---|---|---|---|
| 8,871,159 B1 * | 10/2014 | Apfel | G01N 1/286 422/536 |
| 8,883,499 B2 * | 11/2014 | Hedrick | A61B 17/00 424/93.7 |
| 9,144,583 B2 * | 9/2015 | Ariff | A61K 35/12 |

FOREIGN PATENT DOCUMENTS

WO    WO-2017112455 A2 *   6/2017   ............ C12M 23/08

OTHER PUBLICATIONS

Gossett et al. (2010) Analytical Bioanalytical Chemistry 397(8): 3249-3267.*
Bhagat et al. (2010) Med. Biol. Eng. Comput. 48(10): 999-1014.*
Lara et al. (2006) Biotechnol. Bioeng. 94(1): 66-80.*
Qiu, et al. (2015) Lab on a Chip 15(1): 339-350. (Year: 2015).*
Triantafillu, et al. (2017) Biotechnol. Progress Ahead of Print. DOI:10.1002/btpr.2528 (Year: 2017).*

* cited by examiner

*Primary Examiner* — Lisa J Hobbs
(74) *Attorney, Agent, or Firm* — Meunier Carlin & Curfman LLC

(57) ABSTRACT

Various implementations include systems and methods for automatically and continuously dissociating spheres of cells. In particular, one such system includes a peristaltic pump in fluid communication via tubing with a bioreactor in which cells are cultivated. A plurality of conduits are disposed within a portion of the tubing such that fluid flowing between the bioreactor and the pump passes through the conduits. The conduits have an inner diameter that is sized to provide a shear stress to the fluid of between about 5 to about 60 dynes/cm$^2$, which is sufficient for dissociating the spheres of cells passing through the conduits. For example, each conduit may have an inner diameter of between about 50 and about 250 micrometers.

18 Claims, 6 Drawing Sheets

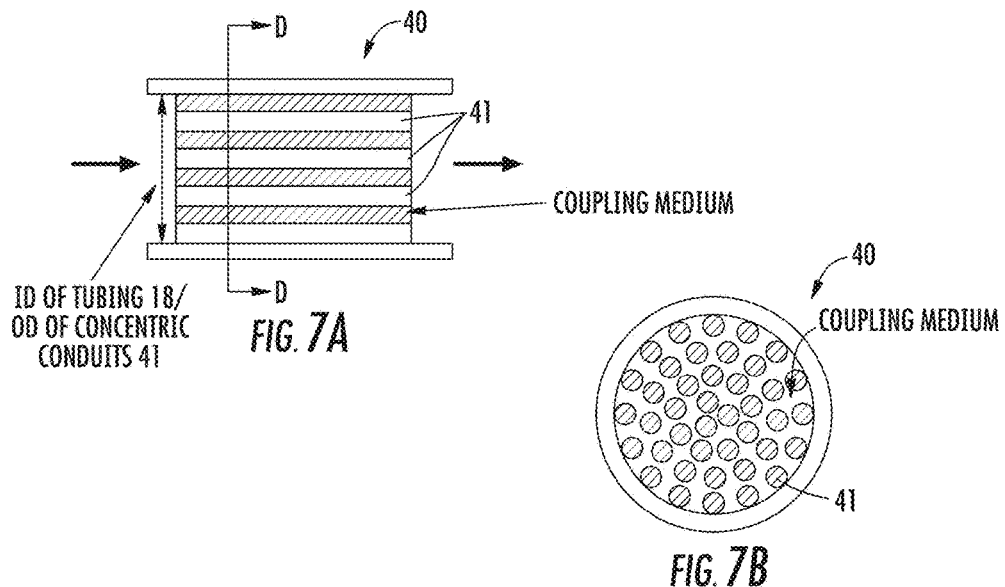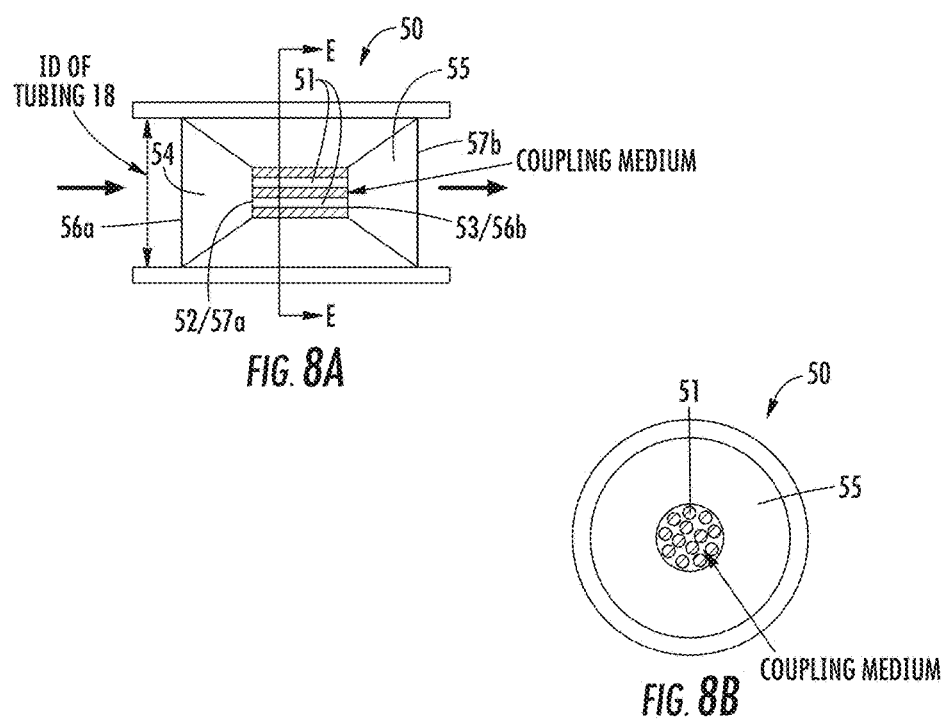

SYSTEMS AND METHODS OF DISSOCIATING AGGREGATE SPHERES OF CELLS

CROSS REFERENCE TO RELATED APPLICATIONS

This application claims priority to U.S. Provisional Patent Application No. 62/015,082 entitled "Systems and Methods of Dissociating Aggregate Spheres of Cells," filed Jun. 20, 2014, the content of which is herein incorporated by reference in its entirety.

ACKNOWLEDGEMENT OF GOVERNMENT SUPPORT

This invention was made with government support under grant no. 1342388 awarded by National Science Foundation. The government has certain rights in this invention.

BACKGROUND

The hope for stem cell-based regenerative medicine is closer to reality than ever before. Recently, the Nobel Prize was awarded for the technology to generate induced pluripotent stem cells (iPSCs). As the name suggests, we can now induce non-embryonic cell sources to become stem cell-like, which could in turn be differentiated into specific cell types and even whole organs for regenerative medicine. Among many advantages this brings, this technology can help circumvent past ethical dilemmas surrounding the use of embryonic stem cells. In addition to iPSCs, human bodies also contain somatic ("adult") stem cells that can be harnessed and be similarly coaxed to differentiate into regenerative cells. Commonly used somatic stem cells include the mesenchymal stem cells and neural stem cells. Regardless of the type, the new looming technical challenge is to generate an appreciate quantity of these therapeutic stem cells.

In addition to therapeutic stem cells, there is also a growing appreciation for the existence of malignant cancer stem cells (CSCs), which are hypothesized to uniquely possess properties of tumor initiation. Experimental evidence for their existence was first provided in leukemia stem cells. Subsequently, similar demonstration was provided for solid tumors including breast, brain, colon, and prostate cancers. Though the observation of tumor initiation in animal models is the current gold standard method of confirming the identity of CSCs, sphere formation and limiting dilution assays are also widely used surrogate in vitro methods of confirming CSC identity. This is based on the theory that a single CSC is sufficient to replicate into aggregates of cell spheres based on its self-renewal properties. Furthermore, it has been shown that cells isolated from resected tumor tissues retain their stemness better when grown as sphere aggregates in vitro, which is the same manner in which the aforementioned therapeutic stem cells are grown. Because CSCs are rare and difficult to acquire, there is a desire to expand them to advance oncology research, but this has been difficult and challenging.

For both therapeutic stem cells and malignant CSCs (collectively referred to henceforth as "stem cells"), the aggregates must be dissociated into single cells once grown to a critical sphere diameter. When spheres become too large, inadequate nutrient and oxygen supplies can cause premature necrotic cell death and negate the efforts to increase their number. Currently, this is a labor-intensive and time-consuming manual process that require physical trituration of the aggregates through a small orifice of pipette tips. In addition, it is unclear how such repeated shear stress affects the stem cells and how many of them survive the rather harsh processing.

Thus, there is a need in the art for a continuous and automated process for dissociating spheres of cells.

BRIEF SUMMARY

Various implementations include systems and methods for automatically and continuously dissociating spheres of cells. In particular, one such system includes a peristaltic pump in fluid communication via tubing with a bioreactor in which cells are cultivated. A plurality of conduits are disposed within a portion of the tubing such that fluid flowing between the bioreactor and the pump passes through the conduits. The conduits have an inner diameter that is sized to provide a shear stress to the fluid of between about 5 to about 60 dynes/cm$^2$, which is sufficient for dissociating the spheres of cells passing through the conduits. For example, each conduit may have an inner diameter of between about 50 and about 250 micrometers.

For example, certain implementations include a device for dissociating aggregate spheres of cells into single cells. The device includes a plurality of conduits, and each conduit has an inlet end and an outlet end. The conduits are disposable within the inner diameter of the tubing such that cells flowing through the tubing pass through the inlet ends of the conduits and out of the outlet ends of the conduits. Each conduit imparts a shear stress on the cells flowing there through sufficient to dissociate aggregate spheres of cells.

In some implementations, the inner diameter of each conduit is between about 50 and about 250 micrometers, and each conduit may be formed from polyether ether ketone (PEEK). In addition, the conduits are coupled together. In some implementations, the conduits are spaced apart from adjacent conduits and are held in position relative to each other via a coupling medium that extends between the conduits. For example, the coupling medium may include a fluid impermeable material, such as a silicone adhesive. In other implementations, the conduits are arranged in a touching relationship with adjacent conduits. For example, the touching conduits may have an overall outer diameter that is substantially the same as an inner diameter of a tubing, and in some implementations, the conduits may be held together via a friction fit with the inner diameter of the tubing. Alternatively, the conduits may be coupled together prior to being disposed within the tubing or used without tubing. Furthermore, the shear stress imparted by each conduit may be between about 5 and about 60 dynes/cm$^2$.

In some implementations, the device further includes a frusto-conically shaped inlet conduit and a frusto-conically shaped outlet conduit. Each of the inlet conduit and the outlet conduit has an inlet end and an outlet end, wherein an outer diameter of the inlet end of the inlet conduit and the outlet end of the outlet conduit is substantially the same as the inner diameter of the tubing and is larger than the outlet end of the inlet conduit and the inlet end of the outlet conduit. The plurality of conduits are disposed between the outlet end of the inlet conduit and the inlet end of the outlet conduit such that the outlet end of the inlet conduit is adjacent and in fluid communication with inlet ends of the conduits and the inlet end of the outlet conduit is adjacent and in fluid communication with the outlet ends of the conduits. In some implementations, the inlet and outlet conduits and/or the plurality of conduits are coupled together. For example, the conduits may be coupled together within the inner diameter of the tubing or prior to being inserted into the tubing. The shear stress imparted by the conduits in this arrangement may be between about 5 and about 60 dynes/cm$^2$. Furthermore, the conduits and/or the inlet and outlet conduits may be formed from polyether ether ketone (PEEK).

In some implementations, the tubing is in fluid communication with a pump, such as a peristaltic pump. And, in some implementations, the tubing may be an inlet or an outlet tubing for the pump. Alternatively, the tubing may be in fluid communication with a manually actuated syringe.

According to other implementations, a continuous process for dissociating spheres of cells includes: (1) providing a plurality of conduits into a tubing having an inner diameter, each of the plurality of conduits having an inner diameter that is less than the inner diameter of the tubing, wherein the conduits are configured for imparting shear stresses on at least a portion of the spheres of cells of between about 5 and about 60 dynes/cm$^2$, wherein the tubing extends between and is in fluid communication with a bioreactor containing cells and a pump; and (2) pumping, via the pump, the cells through the tubing and the conduits between the pump and the bioreactor, wherein movement of the cells through the conduits imparts shear stresses on the spheres of cells sufficient to dissociate them into single cells. In some implementations, the pump may be a peristaltic pump. In addition, in some implementations, the tubing may include an inlet tubing through which fluids move into the pump from the bioreactor and an outlet tubing through which fluids move away from the pump toward the bioreactor. The conduits may be disposed within the outlet tubing or the inlet tubing.

BRIEF DESCRIPTION OF THE DRAWINGS

The components in the drawings are not necessarily to scale relative to each other. Like reference numerals designate corresponding parts throughout the several views.

FIG. 7A illustrates a cross-sectional side view of a sphere dissociation device according to another implementation that may be used in the system shown in FIG. 4. The cross sectional side view is taken through the A-A line in FIG. 4.

FIG. 7B illustrates a cross-sectional front view of the device shown in FIG. 7A as taken through the D-D line in FIG. 7A.

FIG. 8A illustrates a cross-sectional side view of a sphere dissociation device according to another implementation that may be used in the system shown in FIG. 4. The cross sectional side view is taken through the A-A line in FIG. 4.

FIG. 8B illustrates a cross-sectional front view of the device shown in FIG. 8A as taken through the E-E line in FIG. 8A.

DETAILED DESCRIPTION

Various implementations include systems and methods for automatically and continuously dissociating spheres of cells. In particular, one such system includes a peristaltic pump in fluid communication via tubing with a bioreactor in which cells are cultivated. A plurality of conduits are disposed within a portion of the tubing such that fluid flowing between the bioreactor and the pump passes through the conduits. The conduits have an inner diameter that is sized to provide a shear stress to the fluid of between about 5 to about 60 dynes/cm$^2$, which is sufficient for dissociating the spheres of cells passing through the conduits. For example, each conduit may have an inner diameter of between about 50 and about 250 micrometers.

Various implementations of the system use existing pump and fluid flow systems to provide the continuous and automatic dissociation of aggregate spheres of cells, making it easily implementable. In particular, the systems and methods described herein are well suited for cell cultures performed in suspension and/or continuous flow.

Figure 1:
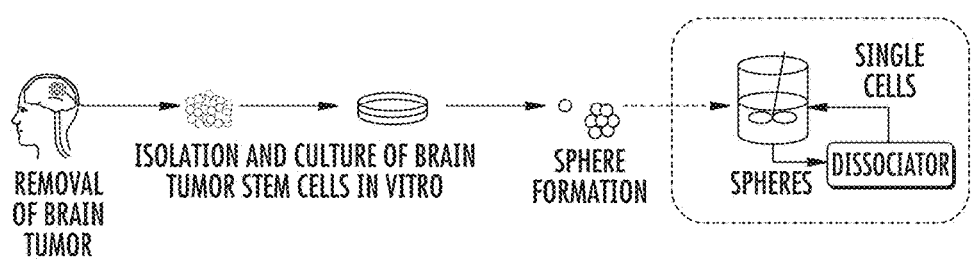
FIG. 1 illustrates a schematic of a process of obtaining an in vitro stem cell culture.
Figure 2:
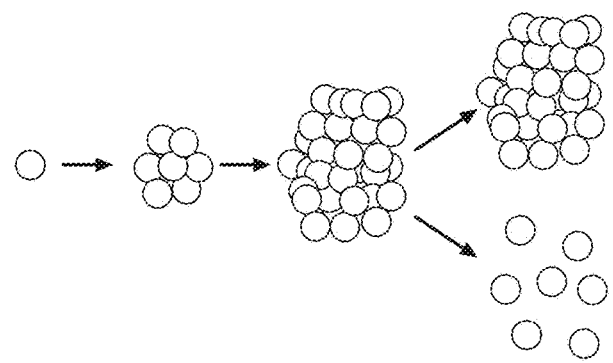
FIG. 2 illustrates a schematic process of a stem cell aggregating and then being dissociated.
Figure 3:
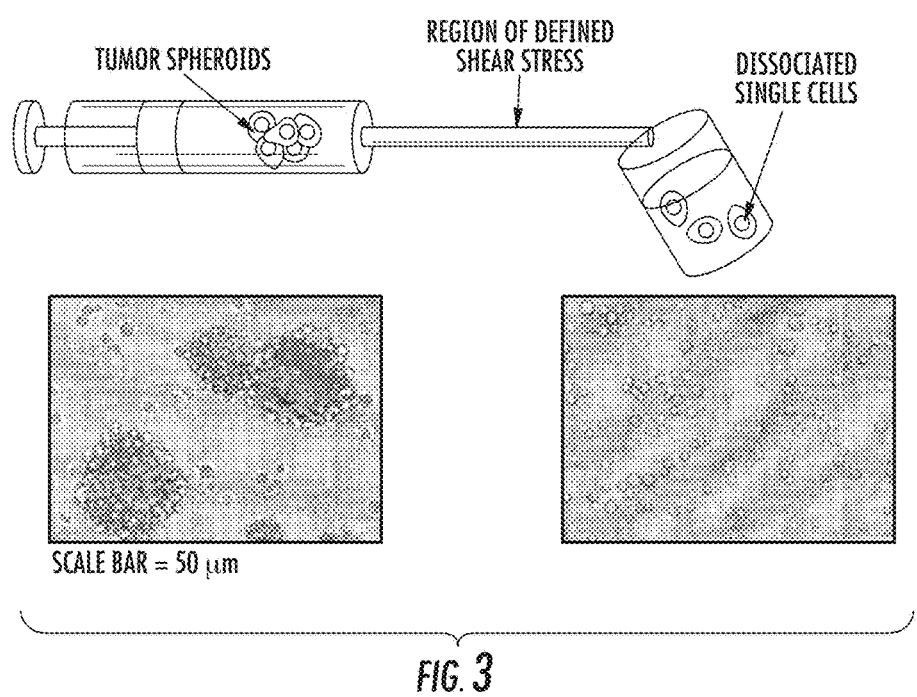
FIG. 3 illustrates a schematic of a manual process of dissociating stem cells with a pipette.

FIG. 1 illustrates a schematic of a process of obtaining an in vitro stem cell culture for a brain tumor stem cell according to one implementation. As shown, a brain tumor is removed, the brain tumor stem cells are isolated and cultured in vitro, spheres are formed in a bioreactor, and the spheres are dissociated via a dissociation device that is in fluid communication with a bioreactor. FIG. 2 illustrates a schematic process of a stem cell aggregating and then being dissociated. As noted above, dissociation of the spheres is currently performed using a manual process with a pipette, which is illustrated in FIG. 3. The spheroids are drawn into the pipette, and upon being pushed out, the spheroids are subjected to sufficiently high shear stress as they exit the pipette, which dissociates the spheroids. However, this process is very time consuming.

Figure 4:
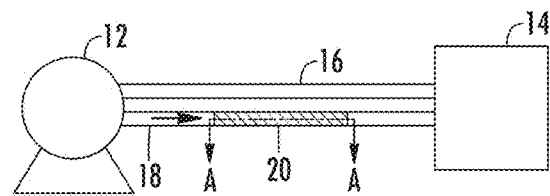
FIG. 4 illustrates a schematic of an automated sphere dissociation system according to one implementation.

The inventors have developed improved devices and methods for automatically dissociating spheroids. FIG. 4 illustrates a schematic of an automated sphere dissociation system according to one implementation. The system 10 includes a peristaltic pump 12, a bioreactor 14, and tubing 16, 18 that extends between and is in fluid communication with the pump 12 and the bioreactor 14. The tubing 16 is inlet tubing through which fluid flows from the bioreactor 14 to the pump 12, and the tubing 18 is outlet tubing through which fluid flows from the pump 12 to the bioreactor 14. A dissociation device 20 is disposed within the outlet tubing 18. However, in alternative implementations, the dissociation device 20 may be disposed within the inlet tubing 16.

Figure 5A:
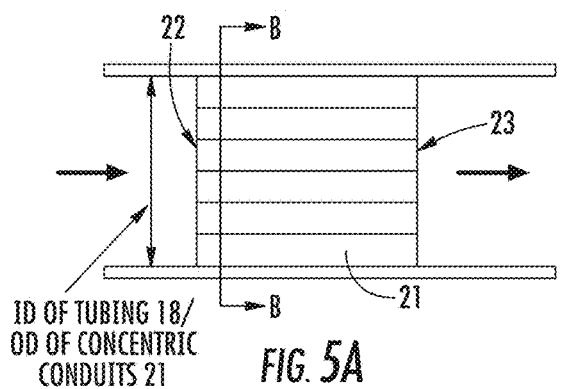
FIG. 5A illustrates a cross-sectional side view of a sphere dissociation device according to one implementation that may be used in the system shown in FIG. 4. The cross sectional side view is taken through the A-A line in FIG. 4.
Figure 5B:
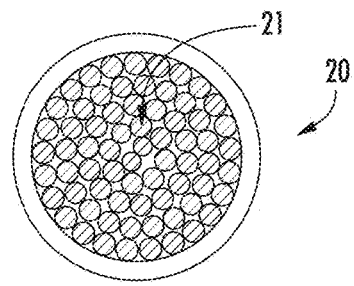
FIG. 5B illustrates a cross-sectional front view of the device shown in FIG. 5A as taken through the B-B line in FIG. 5A.

FIG. 5A illustrates a side cut out view of the dissociation device 20 along the A-A line in FIG. 4 according to one implementation. FIG. 5B illustrates a cross sectional view of the device 20 as taken through the B-B line in FIG. 5A. In particular, the device 20 includes a plurality of conduits 21. The conduits 21 are arranged in a touching relationship with adjacent conduits. Each conduit 21 has an inlet end 22 and an outlet end 23. The plurality of conduits 21 has an overall outer diameter that is substantially the same as an inner diameter of the outlet tubing 18. For example, in various implementations in which the outer diameter of each conduit 21 is about 360 micrometers and the inner diameter of the outlet tubing 18 is about 0.8 millimeters, 3 conduits 21 may be disposed within the outlet tubing 18. As another example, for an implementation in which the outer diameter of each conduit is 360 micrometers and the inner diameter of the outlet tubing 18 is about 3.2 millimeters, 59 conduits 21 may be disposed within the outlet tubing 18. The conduits 21 are disposed within the inner diameter of the outlet tubing 18 and held in place via a friction fit. Cells flowing through the tubing 18 pass through the inlet ends 22 of the conduits 21 and out of the outlet ends 23 of the conduits 21, and each conduit 21 imparts a shear stress on the cells flowing there through sufficient to dissociate aggregate spheres of cells.

An inner diameter of each conduit 21 is chosen based on the shear stress that would be sufficient to break up the spheroids into individual cells. For example, the inner diameter of each conduit may be between about 50 and about 250 micrometers. The shear stress imparted by each conduit 21 on the spheroids passing through them is between about 5 and about 60 dynes/cm², which is about 0.5 to about 6 N/m² (or Pa).

In addition, the conduits may be coupled together prior to being disposed within the outlet tubing 18. For example, a thin film may be laminated around at least a portion of the conduits 21 to hold them in their arrangement. Alternatively, the conduits 21 may be used without tubing to dissociate spheroids or within other types of tubing, such as tubing of a manually operated syringe, for example.

The conduits 21 may be extruded from polyether ether ketone (PEEK) or other suitable non adherent polymeric material. In addition, the conduits 21 may be formed by another suitable means. Once formed, the conduits 21 may be cut to length based on how the device 20 is to be used. For example, the length of the conduits 21 in one exemplary implementation was around 45 centimeters, but the conduits may be of greater or lesser length in other implementations.

Figure 6A:
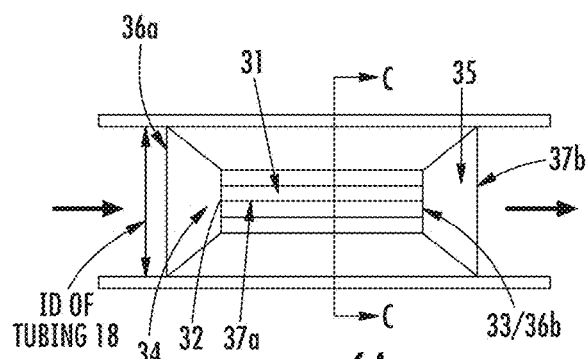
FIG. 6A illustrates a cross-sectional side view of a sphere dissociation device according to another implementation that may be used in the system shown in FIG. 4. The cross-sectional side view is taken through the A-A line in FIG. 4.
Figure 6B:
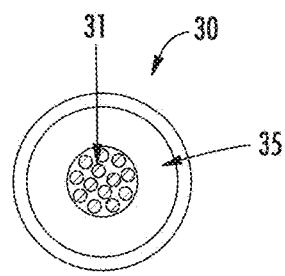
FIG. 6B illustrates a cross-sectional front view of the device shown in FIG. 6A as taken through the C-C line in FIG. 6A.

FIGS. 6A and 6B illustrate a dissociation device 30 according to another implementation. The device 30 may be disposed in the outlet tubing 18 or the inlet tubing 16. In particular, the device 30 includes a plurality of conduits 31, and each conduit has an inner diameter of between about 50 and about 250 micrometers, an inlet end 32, and an outlet end 33. As with device 20, cells flowing through the tubing 16, 18 pass through the inlet ends 32 of the conduits 31 and out of the outlet ends 33 of the conduits 31, and each conduit 31 imparts a shear stress on the cells flowing there through sufficient to dissociate aggregate spheres of cells.

The device 30 also includes a frusto-conically shaped inlet conduit 34 and a frusto-conically shaped outlet conduit 35, each of the inlet conduit 34 and the outlet conduit 35 having an inlet end 36a, 36b and an outlet end 37a, 37b, respectively. An outer diameter of the inlet end 36a of the inlet conduit 34 and the outlet end 37b of the outlet conduit 35 is substantially the same as the inner diameter of the tubing 18 and is larger than the outlet end 37a of the inlet conduit 34 and the inlet end 36b of the outlet conduit 35. The plurality of conduits 31 are disposed between the outlet end 37a of the inlet conduit 34 and the inlet end 36b of the outlet conduit 35 such that the outlet end 37a of the inlet conduit 34 is adjacent and in fluid communication with inlet ends 32 of the conduits 31 and the inlet end 36b of the outlet conduit 35 is adjacent and in fluid communication with the outlet ends 33 of conduits 31. In one implementation, the inlet 34 and outlet conduits 35 and the plurality of conduits 31 are coupled together, such as by using a thin polymer film or adhesive, prior to being disposed within the tubing 18. In addition, the conduits 31 may be used without tubing to dissociate spheroids or within other types of tubing, such as tubing of a manually operated syringe, for example.

Similar to the conduits 21 described above in relation to FIGS. 5A and 5B, the conduits 31 may impart a shear stress of between about 5 and about 60 dynes/cm², which is about 0.5 to about 6 N/m² (or Pa). And, the conduits 31 and the inner 34 and outer frusto-conical shaped conduits 35 may be formed from polyether ether ketone (PEEK) or other suitable material.

FIGS. 7A and 7B illustrate a dissociation device 40 according to another implementation. The device 40 is similar to the device 20 shown in FIGS. 5A and 5B, but the conduits 41 are arranged in a spaced apart relationship relative to adjacent conduits 41. In particular, the conduits 41 are radially spaced apart from each other (not touching). The conduits 41 may be held in place by a coupling medium 45. In some implementations, the coupling medium 45 may include a fluid impermeable material. For example, the coupling medium 45 may be a silicone adhesive, another type of adhesive, a resin, or another suitable material. In addition, the coupling medium may be disposed adjacent the conduits 41 by pouring the coupling medium in its liquid state into a mold into which the conduits 41 have been disposed and allowing the coupling medium to transform into a solid state. Alternatively, the conduits and coupling medium may be extruded together or separately and assembled together.

Like devices 20, 30, device 40 may be disposed in the outlet tubing 18 or the inlet tubing 16. And, each conduit 41 has an inner diameter of between about 50 and about 250 micrometers, an inlet end 42, and an outlet end 43. As with device 20, cells flowing through the tubing 16, 18 pass through the inlet ends 42 of the conduits 41 and out of the outlet ends 43 of the conduits 41, and each conduit 41 imparts a shear stress on the cells flowing there through sufficient to dissociate aggregate spheres of cells. Similar to the conduits 21, 31 described above in relation to FIGS. 5A through 6B, the conduits 41 may impart a shear stress of between about 5 and about 60 dynes/cm², which is about 0.5 to about 6 N/m² (or Pa). And, the conduits 41 may be formed from polyether ether ketone (PEEK) or other suitable material.

FIGS. 8A and 8B illustrate a dissociation device 50 according to another implementation. The device 50 is similar to the device 30 shown in FIGS. 6A and 6B, but the conduits 51 are arranged in a spaced apart relationship, such as is shown in FIGS. 7A and 7B. In particular, the conduits 51 are spaced apart from each other (not touching). The conduits 51 may be held in place by a coupling medium, such as a fluid impermeable material. For example, the coupling medium may include a silicone adhesive. Like devices 20, 30, 40, device 50 may be disposed in the outlet tubing 18 or the inlet tubing 16. And, each conduit 51 has an inner diameter of between about 50 and about 250 micrometers, an inlet end 52, and an outlet end 53.

Like device 30, device 50 also includes a frusto-conically shaped inlet conduit 54 and a frusto-conically shaped outlet conduit 55, each of the inlet conduit 54 and the outlet conduit 55 having an inlet end 56a, 56b and an outlet end 57a, 57b, respectively. An outer diameter of the inlet end 56a of the inlet conduit 54 and the outlet end 57b of the outlet conduit 55 is substantially the same as the inner diameter of the tubing 18 and is larger than the outlet end 57a of the inlet conduit 54 and the inlet end 56b of the outlet conduit 55. The plurality of conduits 51 are disposed between the outlet end 57a of the inlet conduit 54 and the inlet end 56b of the outlet conduit 55 such that the outlet end 57a of the inlet conduit 54 is adjacent and in fluid communication with inlet ends 52 of the conduits 51 and the inlet end 56b of the outlet conduit 55 is adjacent and in fluid communication with the outlet ends 53 of the conduits 51.

As with device 30, cells flowing through the tubing 16, 18 pass through the inlet ends 52 of the conduits 51 and out of the outlet ends 53 of the conduits 51, and each conduit 51 imparts a shear stress on the cells flowing there through sufficient to dissociate aggregate spheres of cells. Similar to the conduits 21, 31, 41 described above in relation to FIGS. 5A through 7B, the conduits 51 may impart a shear stress of between about 5 and about 60 dynes/cm$^2$, which is about 0.5 to about 6 N/m$^2$ (or Pa). And, the conduits 51 and the inner 54 and outer frusto-conical shaped conduits 55 may be formed from polyether ether ketone (PEEK) or other suitable material All four devices 20, 30, 40, 50 may be useful in the dissociation system. The following discussion includes some exemplary advantages and disadvantages to each device. In the field, the selection of which device 20, 30, 40, 50 to use in the system 10 may be made based on the type of cells being dissociated. For example, device 20 may be more favorable for cell lines that are more sensitive to rapid increases in shear stress or pressure, and devices 30, 40, and 50 may be more favorable if the homogeneity of applied stress and/or degree of dissociation are particularly important. In particular, device 20 includes more conduits than the devices 30, 40, and 50, which offers a larger surface area for shear to occur. In addition, the construction of device 20 may be simpler. And, entrance into the tubes for devices 20 and 40 is straight rather than tapered, which may result in less collision between cells and the inlet ends 22, 42 of the conduits 21, 41, respectively.

However, the velocity profile of the fluid entering the devices 20, 40 is parabolic, which results in the conduits 21, 41 disposed radially outwardly from a center of the tubing 18 having a lower flow rate than those conduits 21, 41 disposed closer to the center of the tubing 18. This arrangement could lead to clogging issues. In addition, the cells passing through the radially outwardly disposed conduits 21, 41 experience less shear stress than those passing through the radially inwardly disposed conduits 21, which may result in a more heterogeneous mixture of single cells and spheres at the outlet ends 23 of the conduits 21. Furthermore, the cells may accumulate at inlet ends 22, 42 of the conduits 21, 41 disposed adjacent a bottom of the tubing 18 due to gravity and lower fluid flow rate in this region.

The tapered inlet 34, 54 and outlet conduits 35, 55 of devices 30 and 50, respectively, allow for more uniform fluid flow and shear conditions through the conduits 31, 51. In addition, the tapered inlet 34, 54 and outlet conduits 35, 55 reduce the possibility of a dead zone adjacent the inlet ends 32, 52 of the conduits 31, 51. Furthermore, high pressure at the inlet ends 32, 52 of the conduits 31, 51 drives more cells into the conduits 31, 51, resulting in less opportunity for the cells to clog.

However, the shear surface area is smaller in devices 30, 40, 50 than in device 20 due to the smaller number of conduits 31, 41, 51. In addition, the design of devices 30 and 50 is more detailed than device 20 and involves the use of special tools and techniques to make the tapered inlet 34, 54 and outlet conduits 35, 55. Furthermore, changes in design parameters, such as the number of conduits 31, 51 or the diameter of each conduit 31, 51, are more difficult to implement than with device 20. And, the pressure increase at the inlet ends 32, 52 of the conduits 31, 51 may be detrimental to cell survival for some cells.

Furthermore, coupling the conduits 41, 51 of devices 40, 50 may be easier in some aspects than with conduits 21, 31 of devices 20, 30. However, devices 40, 50 may have less conduits than devices 20, 30, and therefore may be less efficient and result in decreased homogeneity in some situations.

To use the devices 20, 30, 40, 50 with the pump 12 and the bioreactor 14 to continuously and automatically dissociate spheres of cells into single cells, the device 20, 30, 40, 50 is disposed within the inlet 16 or outlet tubing 18 extending between the pump 12 and the bioreactor 14. The pump 12 causes fluid from the bioreactor 14 to move through the pump and the tubing 16, 18, which forces the fluid through the conduits 21, 31, 41, 51 disposed in the tubing 16, 18. This movement through the conduits 21, 31, 41, 51 imparts shear stresses on spheres of cells sufficient to dissociate them into single cells. The dissociated cells are then returned to the bioreactor 14.

Figure 9:
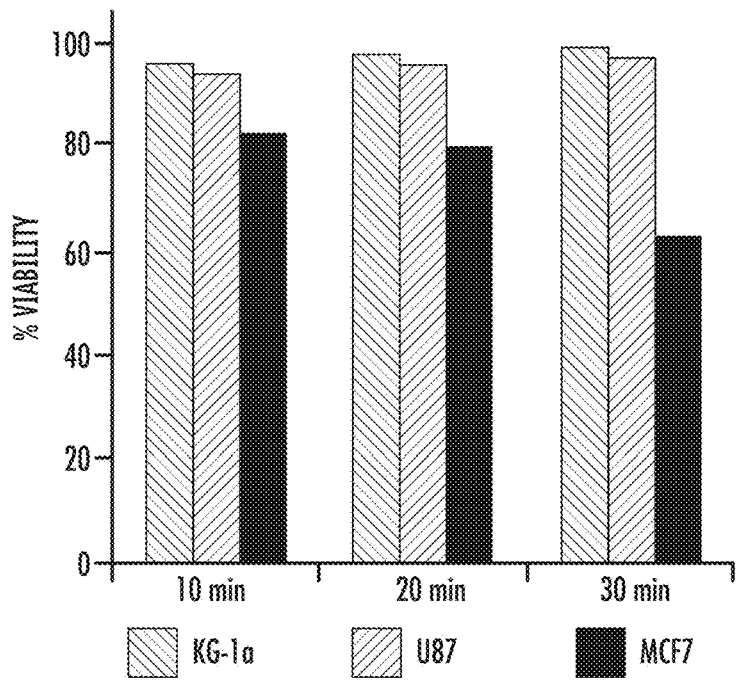
FIG. 9 illustrates a graph showing the percentage of viable cells recovered after subjecting three types of cells to dissociation through a single conduit having an inner diameter of about 125 microns for three time periods.

FIG. 9 illustrates a graph showing the percentage of viable cells recovered after subjecting three types of cells to dissociation through a single conduit having an inner diameter of about 125 microns for three time periods. The three types of cells used in this test included KG-1a (leukemia), which is shown by the gray bar, U87 (glioblastoma), which is shown by the black bar, and MCF7 (breast tumor), which is shown by the white bar. The three time periods were 10 minutes, 20 minutes, and 30 minutes, and the shear stress imparted by the conduits was about 20 dynes/cm$^2$. As shown in FIG. 9, the breast tumor cells had less viable cells after being passed through the conduit than the other two types of cells, which suggests that these cells are more sensitive to shear stress than the other two types of cells. Thus, another advantage to the device 20 (and device 30) is that shear-tolerant cells may be distinguished from shear-sensitive cells.

Figure 10:
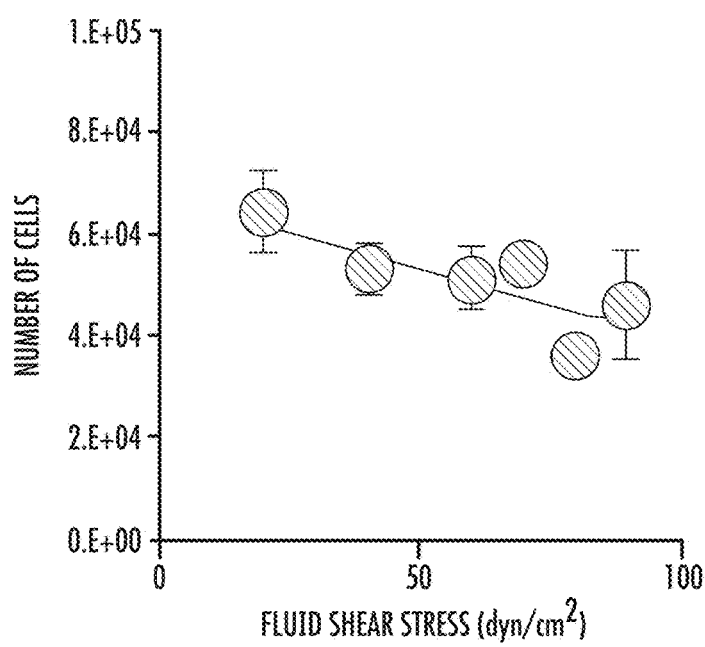
FIG. 10 illustrates a graph showing the number of cells recovered after subjecting cells to varying levels of shear stress through a single conduit having an inner diameter of about 125 microns.

FIG. 10 illustrates a graph showing the number of cells recovered after subjecting cells to varying levels of shear stress through a single conduit having an inner diameter of about 125 microns. In particular, KG-1a cells were passed through the single conduit at various fluid flow velocities. Cells were collected in intervals and tested for viability. The various fluid flow velocities imparted a shear stress of between about 5 dynes/cm$^2$ to about 90 dynes/cm$^2$. As shown in FIG. 10, the number of viable cells collected after passing through the conduit decreased somewhat inversely proportional to increases in shear stress. However, the amount of viable cells remaining after passing through the conduit at shear stresses up to 90 dynes/cm$^2$ may still be sufficient.

Figure 11:
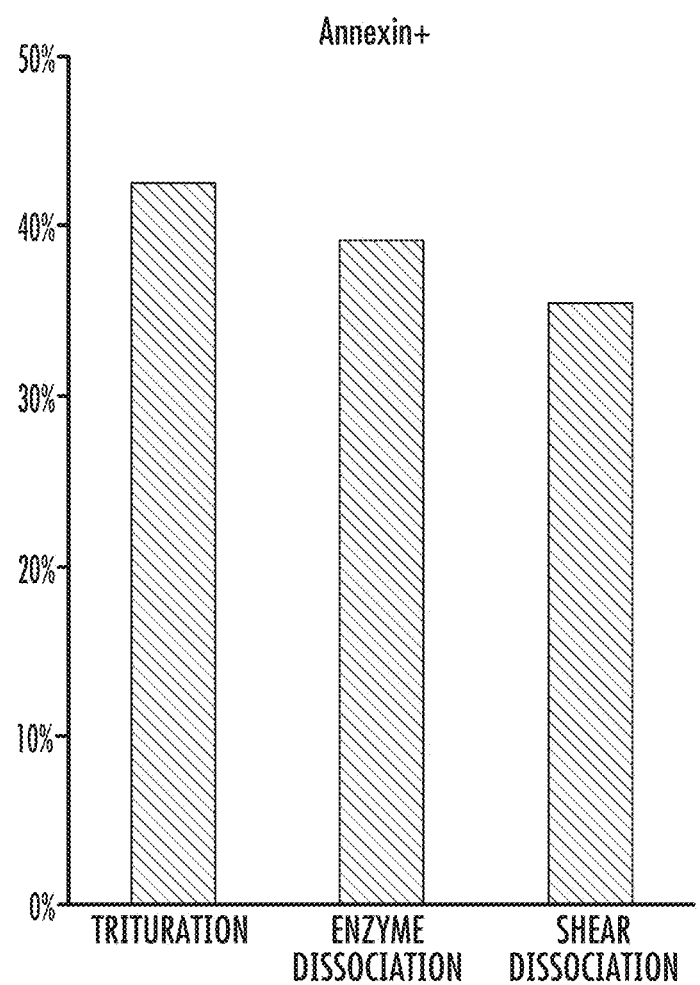
FIG. 11 illustrates a graph showing levels of annexin in cells using various methods of dissociation according to one implementation.

FIG. 11 illustrates a comparison of annexin levels in cells using various dissociation methods, including pipette trituration, Accutase enzyme dissociation, and shear dissociation using device 40. Annexin is a marker for apoptosis programmed cell death. As shown in FIG. 11, there was a lowered number of cells positive for annexin using the shear dissociation device 40 device as compared to the other dissociation methods.

The devices recited in the appended claims are not limited in scope by the specific devices and methods of using the same described herein, which are intended as illustrations of a few aspects of the claims. Any devices or methods that are functionally equivalent are intended to fall within the scope of the claims. For example, the above described implementations describe the device as being disposable within tubing in fluid communication with a pump. However, in other implementations, the device may be configured to be used on its own or it may be disposable within tubing of other devices, such as a manually operated syringe, for example.

Various modifications of the devices and methods in addition to those shown and described herein are intended to fall within the scope of the appended claims. Further, while only certain representative devices and method steps disclosed herein are specifically described, other combinations of the devices and method steps are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Those skilled in the art who review this disclosure will readily appreciate that many modifications are possible (e.g., variations in sizes, dimensions, structures, shapes and proportions of the various elements, values of parameters, mounting or layering arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. Other substitutions, modifications, changes and omissions may also be made in the design, operating conditions and arrangement of the various exemplary embodiments without departing from the scope of the present embodiments.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A device for dissociating aggregate spheres of cells in a cell culture media into single cells, the device comprising:
   a tubing for being in fluid communication with a pump and a bioreactor, the tubing having an inlet end and an outlet end and a central axis that extends between the inlet end and the outlet end; and
   a plurality of conduits, each conduit having an inlet end and an outlet end and a central axis that extends between the inlet and outlet ends, wherein the conduits are disposed within an inner diameter of the tubing such that a plane extends transversely through the central axes of the conduits and the tubing and the central axes of each conduit are parallel to each other and the central axis of the tubing,
   wherein:
      an inner diameter of each conduit is between 50 and 250 micrometers, the inner diameter of each conduit imparting a shear stress on the spheres of cells in the cell culture media of between 5 and 60 dynes/cm$^2$, the shear stress being sufficient to dissociate the spheres of cells into single, dissociated cells as the spheres of cells in the cell culture media flow from the inlet end of each conduit to the outlet end of each conduit, wherein the flow through the conduits is caused by a motive force provided by a pump coupled to the tubing, and
      the outlet ends of the conduits are disposed axially inwardly from the outlet end of the tubing such that the single, dissociated cells and culture media flow from the outlet ends of the conduits into the tubing and then through the outlet end of the tubing.

2. The device of claim 1, wherein the conduits are coupled together prior to being disposed within the tubing.

3. The device of claim 2, wherein external surfaces of the conduits are radially spaced apart from external surfaces of adjacent conduits within the inner diameter of the tubing and are held in position relative to each other via a coupling medium that extends radially between the conduits.

4. The device of claim 3, wherein the coupling medium is a fluid impermeable material.

5. The device of claim 4, wherein the coupling medium is a silicone adhesive.

6. The device of claim 2, wherein external surfaces of the conduits are arranged in a touching relationship with external surfaces of radially adjacent conduits.

7. The device of claim 6, wherein the plurality of conduits have an overall outer diameter that is substantially the same as the inner diameter of the tubing.

8. The device of claim 7, wherein the conduits are held within the inner diameter of the tubing via a friction fit.

9. The device of claim 1, further comprising a frusto-conically shaped inlet conduit and a frusto-conically shaped outlet conduit, each of the inlet conduit and the outlet conduit having an inlet end and an outlet end, wherein an outer diameter of the inlet end of the inlet conduit and an outer diameter of the outlet end of the outlet conduit are substantially the same as the inner diameter of the tubing and are larger than the outlet end of the inlet conduit and the inlet end of the outlet conduit, and the plurality of conduits are disposed between the outlet end of the inlet conduit and the inlet end of the outlet conduit such that the outlet end of the inlet conduit is adjacent and in fluid communication with inlet ends of the conduits and the inlet end of the outlet conduit is adjacent and in fluid communication with the outlet ends of the conduits.

10. The device of claim 9, wherein the inlet and outlet conduits and the plurality of conduits are coupled together.

11. The device of claim 1, wherein the pump comprises a peristaltic pump.

12. The device of claim 1, wherein the tubing comprises an inlet or an outlet tubing for the pump.

13. A continuous process for dissociating aggregate spheres of cells in a cell culture media into single, dissociated cells, the process comprising:
   disposing a plurality of conduits into an inner diameter of a tubing, each of the plurality of conduits having an inner diameter that is less than the inner diameter of the tubing, wherein the inner diameter of each of the conduits is between 50 to 250 micrometers; and pumping, via a pump that is in fluid communication with the tubing, aggregate spheres of cells in the culture media through the tubing and the conduits, the pumping causing at least one of the conduits to impart a shear stress on respective aggregate spheres of cells flowing therethrough of between 5 and 60 dynes/cm$^2$, the shear stress on the spheres of cells causing the spheres of cells to dissociate into single, dissociated cells, wherein each conduit has an inlet end and an outlet end and a central axis that extends between the inlet and outlet ends, and the conduits are disposed within the inner diameter of the tubing such that the inlet ends of the conduits are adjacent an inlet end of the tubing and the outlet ends of the conduits are adjacent an outlet end of the tubing and the central axes of each conduit are parallel to each other and a central axis of the tubing, and a plane extends transversely through the central axes of the conduits and the tubing, and wherein the pumping causes the aggregate spheres of cells and cell culture media to flow into the inlet ends of the tubing and conduits, and single, dissociated cells and culture media to flow from the outlet ends of the conduits into the tubing and then through the outlet end of the tubing.

14. The method of claim 13, wherein the tubing comprises an inlet tubing through which fluids move into the pump from the bioreactor and an outlet tubing through which fluids move away from the pump towards the bioreactor, and the conduits are disposed within the outlet tubing.

15. The method of claim 13, wherein external surfaces of the conduits are radially spaced apart from external surfaces of adjacent conduits and are held in position relative to each other via a coupling medium that extends between the conduits.

16. The method of claim 13, wherein the conduits are coupled together prior to being disposed within the tubing.

17. The method of claim 13, further comprising providing a frusto-conically shaped inlet conduit and a frusto-conically shaped outlet conduit, each of the inlet conduit and the outlet conduit having an inlet end and an outlet end, wherein an outer diameter of the inlet end of the inlet conduit and the outlet end of the outlet conduit is substantially the same as the inner diameter of the tubing and is larger than the outlet end of the inlet conduit and the inlet end of the outlet conduit, and the plurality of conduits are disposed between the outlet end of the inlet conduit and the inlet end of the outlet conduit such that the outlet end of the inlet conduit is adjacent and in fluid communication with inlet ends of the conduits and the inlet end of the outlet conduit is adjacent and in fluid communication with the outlet ends of the conduits.

18. The method of claim 13, wherein external surfaces of the conduits are arranged in a touching relationship with external surfaces of radially adjacent conduits.

\* \* \* \* \*